United States Patent [19]

Bax

[11] 4,200,797
[45] Apr. 29, 1980

[54] CONTINUOUSLY ROTATING CAT SCANNING APPARATUS AND METHOD

[75] Inventor: Ronald F. Bax, Columbia, Md.

[73] Assignee: Pfizer Inc., New York, N.Y.

[21] Appl. No.: 959,625

[22] Filed: Nov. 13, 1978

[51] Int. Cl.² ............................................. G03B 41/16
[52] U.S. Cl. ............................... 250/402; 250/445 T;
    250/523
[58] Field of Search ............... 250/522, 523, 401, 402,
    250/439 R, 444, 445, 446, 447, 448, 449, 490

[56] References Cited
U.S. PATENT DOCUMENTS 3,432,657  3/1969  Slavin ................................. 250/490

Primary Examiner—Craig E. Church
Attorney, Agent, or Firm—Cushman, Darby & Cushman

[57] ABSTRACT

A tomographic scanner with a continuously rotating source of radiation is energized by converting inertial mechanical energy to electrical energy. The mechanical-to-electrical conversion apparatus is mounted with the X-ray source to be energized on a rotating flywheel. The inertial mechanical energy stored in the rotating conversion apparatus, flywheel and X-ray source is utilized for generating electrical energy used, in turn, to energize the X-ray source.

38 Claims, 5 Drawing Figures

CONTINUOUSLY ROTATING CAT SCANNING APPARATUS AND METHOD

This invention is generally directed to method and apparatus for generating a rotating beam of penetrating radiation. More particularly, this invention is directed to a computerized axial tomographic (CAT) scanner which utilizes such apparatus and method.

CAT scanners of various designs have now been commercially-available for several years. These scanners measure the transmission/absorption of penetrating radiation along a great number of different paths through a cross-section of an object or patient taken at virtually every possible angle through the cross-section. The data resulting from such measurements is digitized and manipulated according to complex mathematical formulae in an appropriately designed and/or programmed special and/or general purpose computer. The result of such mathematical manipulations is an array of numbers which can be used to generate a two-dimensional display representing the relative densities of the materials encountered within the cross-section under examination.

Some of the early CAT scanners translated an aligned X-ray source and detector(s) between incremental rotations of the whole source/detector assembly to generate the requisite set of input data. Others have used solely rotational motion of a fan beam source of X-rays and an oppositely disposed detector array. Sill others have arranged a completely circular fixed array of detectors which are sequentially illuminated by a fan beam of X-ray radiation emanating from a source which is caused to revolve about a circular arc. This latter type of CAT scanner can be exemplified by the embodiment shown in the copending application of Stein et al, Ser. No. 726,556, filed Sept. 27, 1976. The presently preferred exemplary embodiment of this invention constitutes an improvement for the type of CAT scanner described by Stein et al; however, it may also be found to provide advantages for any type of CAT scanner having a rotating source of radiation. It may also be useful in other types of apparatus where it is necessary to generate a rotating beam of penetrating radiation directed inwardly towards the axis of rotation.

As presently constructed, CAT scanners having a rotating source of radiation (a) have used slip rings to supply the source with the necessary electrical energy or (b) have used elongated cables for this purpose in combination with cable take-up reels and the like for accommodating a limited degree of rotational motion by the source.

If cables are used, there are disadvantages in addition to the necessary provision of take-up reels and the like. For example, since only limited rotational motion is permitted, the source and related apparatus which is to be rotated must first be accelerated to the scanning speed and must then subsequently be decelerated after the scan to a standstill. Of course, the whole apparatus must then be reversely operated to attain the initial starting conditions. Furthermore, if all of this apparatus fails to work properly, high voltage electrical cables may be severed to present safety hazards, possible damage to electrical components, and other mechanical problems as will be appreciated.

The use of slip rings to supply the high voltages and currents required by X-ray tubes is similarly subject to disadvantages. For example, it is probably necessary to keep the high voltage slip rings immersed in oil. Even low voltage slip rings (for filament power) are required to pass relatively high currents which is likely to cause more pitting, arcing and other damage to the slip rings and/or brushes. All of these factors require frequent service and/or cause degraded performance of the scanner. These problems are further compounded by the fact that tomographic scanners are presently constructed such that any slip rings employed will necessarily be of a relatively large diameter (e.g., on the order of one meter). Accordingly, if even moderate scanning speeds are employed, the relative surface velocity between the slip rings and brushes will necessarily be rather large, thus, compounding the normal problems to be encountered with the use of slip rings.

Now, however, with this invention, it is possible to avoid the use of *either* slip rings or cables for supplying the radiation source with electrical energy. In brief, this is accomplished by generating the necessary electricity with mechanical-to-electrical conversion means mounted for rotation with the X-ray tube. If the mass embodied in the conversion apparatus and the X-ray tube are continuously rotated, a substantial quantity of inertial mechanical energy will be stored therein. Of course, additional weights mounted on the rotating support member (e.g., a heavy plate may be mounted about the entire cicumference) will similarly store inertial mechanical energy if continuously rotated. The whole mass of rotating components may be thought of as a "flywheel". This stored mechanical energy is then converted (e.g., by an alternator whose shaft is belt driven from a pulley that is fixed with respect to the rotating apparatus) to electrical energy used for activating or energizing the X-ray tube. In this manner, it is unnecessary to transfer any significant amounts of electrical power or energy over electrical cables or slip rings to the rotating X-ray tube. If it is necessary to pass low power signalling information to the rotating apparatus, this may be accomplished with small signal slip rings, optically operated switches, magnetically operated switches, etc.

Besides eliminating problems associated with slip rings or cables and avoiding the necessity to rapidly accelerate and decelerate the X-ray tube, etc., this invention also conveniently provides for storage of the relatively large quantity of energy needed for successfully completing a tomographic scan in a relatively short time period (e.g., less than one second). Furthermore, since the electrical supply for an X-ray tube and/or apparatus used in conjunction with an X-ray tube (e.g., heat exchangers) is relatively heavy, this invention constructively utilizes the mass of these items as energy storage devices in addition to their normal and necessary functions involved in operation of the X-ray tube. Indeed, the mass of the rotating member may itself also be used as a heat sink as well as an energy storage device. In this way the rotating components simultaneously address and solve the energy storage, heat dissipation and electrical energy supply requirements associated with a rapid CAT scanning cycle.

It can be shown that appropriately 75,000 joules of energy are needed to make the data resulting from one tomographic scan statistically acceptable. This requirement is substantially independent of the time period or duration of the scanning cycle. Therefore, if one desired to have relatively short scanning cycles (e.g., less than one second), it becomes apparent that some sort of energy storage scheme is required to avoid unnecessarily large transient loads in normal electrical supply lines and/or to prevent the necessity of using supply circuits designed to handle massive amounts of power. Accordingly, this invention not only overcomes some problems associated with earlier scanners having rotating sources of radiation, it actually facilitates the achievement of relatively short scanning cycles. As will be appreciated, shorter scanning cycles are desired to help "stop" the motion of body organs and thus make tomographic scanning more generally usable throughout the body of a patient.

The CAT scanner of this invention utilizes inertial (flywheel) energy storage. The mass of an electrical generator or alternator, transformer, X-ray tube, counterweights and a rotating mounting member are all utilized as part of the energy storage medium. To extract some of the stored mechanical energy, the alternator (which rotates as a part of the "flywheel") is belt driven by engagement with a stationary pulley. Of course, gears or chains might also be employed.

During a tomographic scan (e.g., one revolution), the rotating apparatus will necessarily slow somewhat as it loses kinetic energy. Accordingly, it might be expected that the voltage output from the alternator would also diminish correspondingly. However, such an expected "droop" in the output of the alternator can be compensated by using suitable voltage and/or current regulating circuits or by making the high voltage transformer resonant at a frequency slightly below the nominal operating frequency of the alternator. Alternatively, a photodetector may be used to actually monitor the X-ray output of the tube and drive a feedback loop which adjusts the system sensitivity to accommodate the actual output of the X-ray tube and/or to drive a voltage/current regulating circuit to help maintain the output of the X-ray tube at desired values.

These as well as other advantages and features of this invention will be more completely understood by reading the following detailed description of an exemplary embodiment of this invention taken in conjunction with the accompanying drawings, of which:

Figure 1:
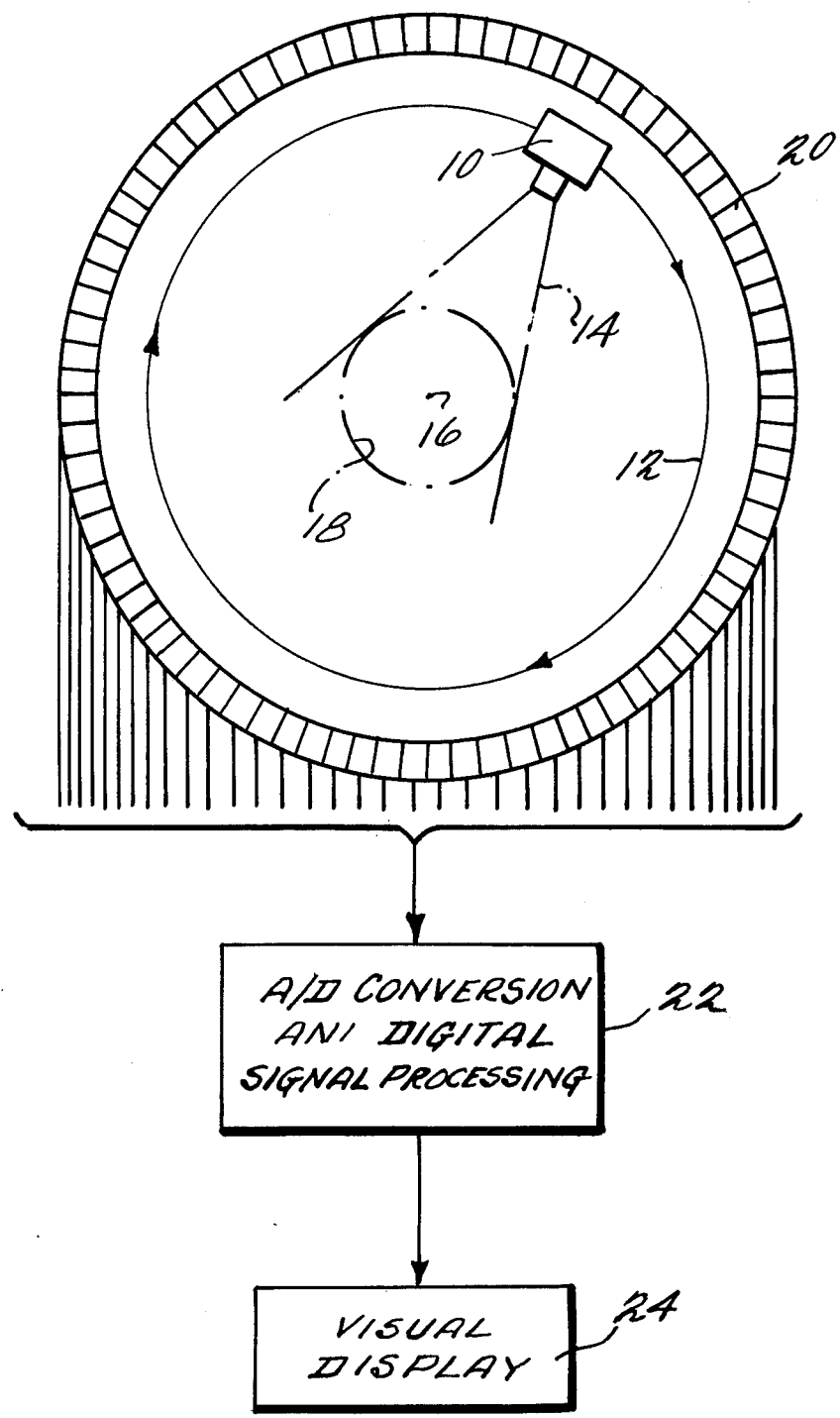
FIG. 1 is a schematic depiction of the type of CAT scanner in which the presently preferred exemplary embodiment may be employed.

A CAT scanner of the type disclosed in the copending application of Stein et al, Ser. No. 726,556, filed Sept. 27, 1976, is schematically depicted in FIG. 1. Such a scanner employs a rotating source of X-rays 10 which revolves about a circular arc 12. A fan-shaped planar beam 14 of penetrating X-ray radiation is inwardly directed towards the axis of rotation 16. This fan-shaped beam 14 substantially encompasses a patient circle or aperture 18 and radiation transmitted through the patient or object situated therein strikes opposingly situated detectors in the fixed circular array of detectors 20. Typically there are on the order of 600 detectors in the array 20 spaced at equal intervals about the circumference of a circle. These detectors may be scintillators which produce photons in response to incident X-rays with the photons being directly or indirectly coupled (e.g., through light pipes) to photomultipliers. Other transducing arrangements may be utilized for obtaining electrical signals representative of the transmitted radiation incident upon the detector sites. Furthermore, since only a portion of the detectors are irradiated at any given time, the optical and/or electrical signal translating and processing circuits may be time multiplexed.

In any event, signals representing transmitted/absorbed radiation from the detector array 20 are converted to digital form, if not already in that form, and conventionally processed at 22 in either special purpose or properly programmed general purpose computing equipment as will be appreciated by those in the art. There are many conventional algorithms for processing this data including those which involve convolution with a suitable digital filter function as will also be appreciated by those in the art. The result of these mathematical manipulations is an array of numbers representing the relative X-ray absorption/transmission taking place in each of many relatively small volumes within the irradiated cross-section of a patient disposed within the patient circle 18. A visual display 24, such as the face of a CRT, is then provided with each pixel of the display having a color or luminance value related to a corresponding numerical entry in the computed array which, in turn, corresponds to a respectively associated incremental volume in the patient's cross-section. The resulting visual display 24 is an axial tomographic view of tissue density within the irradiated cross-section of the patient.

Although the presently preferred exemplary embodiment of this invention is especially suited for use with the type of CAT scanner shown in FIG. 1, it may be advantageously used in any type of CT scanner or other radiation scanning apparatus using a rotating source of radiation.

As described above, the necessary electrical energy for operating the radiation source traditionally has been supplied through slip rings or cables from transformers, rectifiers, etc., which are relatively fixed with respect to the revolving source. Some of the disadvantages which accrue from the use of cables and/or slip rings have already been mentioned.

Figure 2:
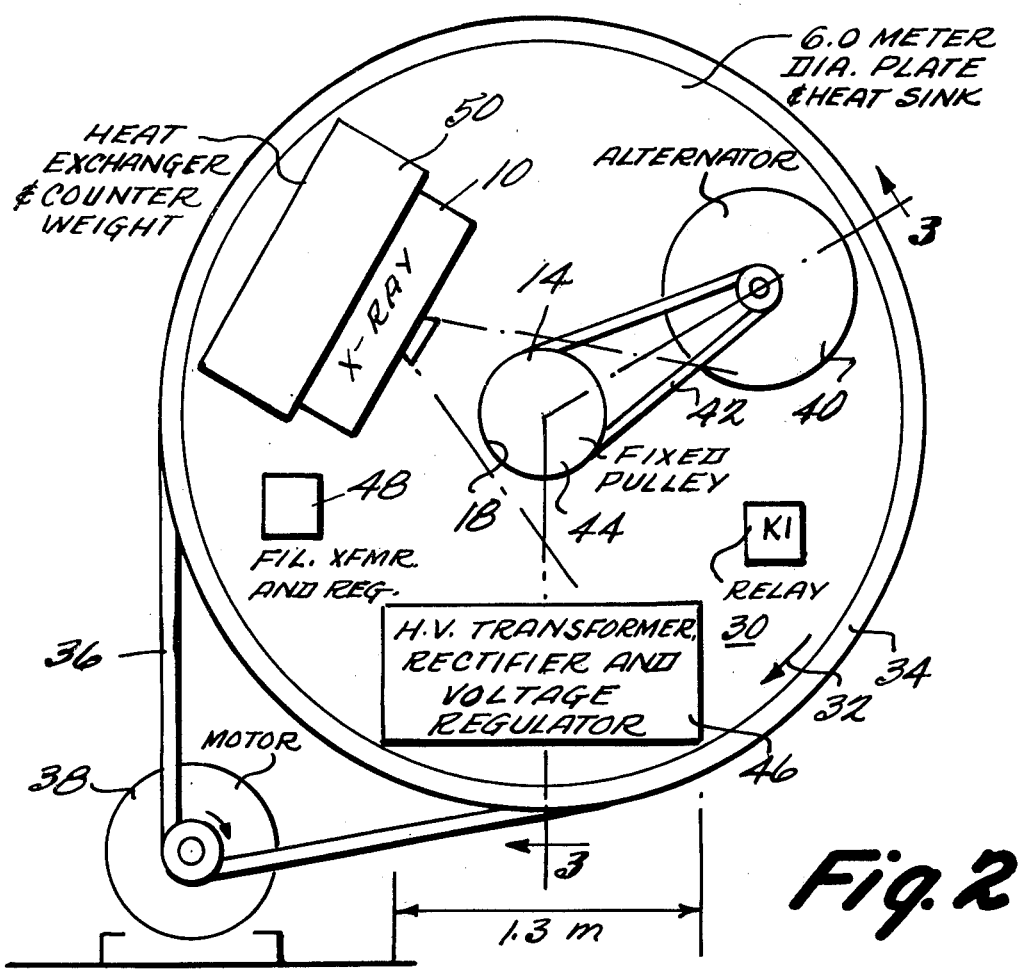
FIG. 2 is a schematic elevational view of the rotating apparatus employed in an exemplary embodiment of this invention and its driving means.
Figure 3:
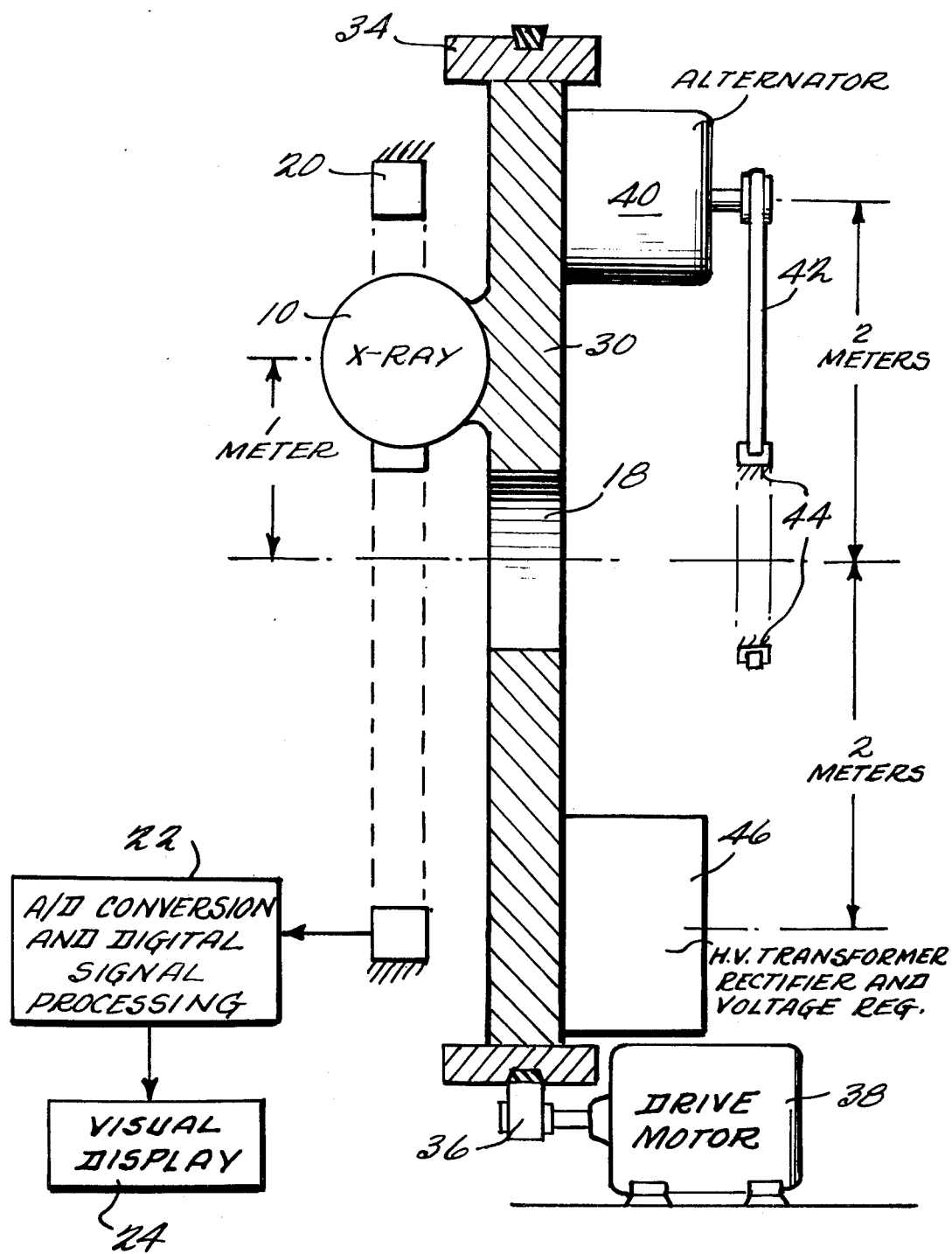
FIG. 3 is a cross-sectional view of the apparatus shown in FIG. 2 taken along the lines 3—3.
Figure 4:
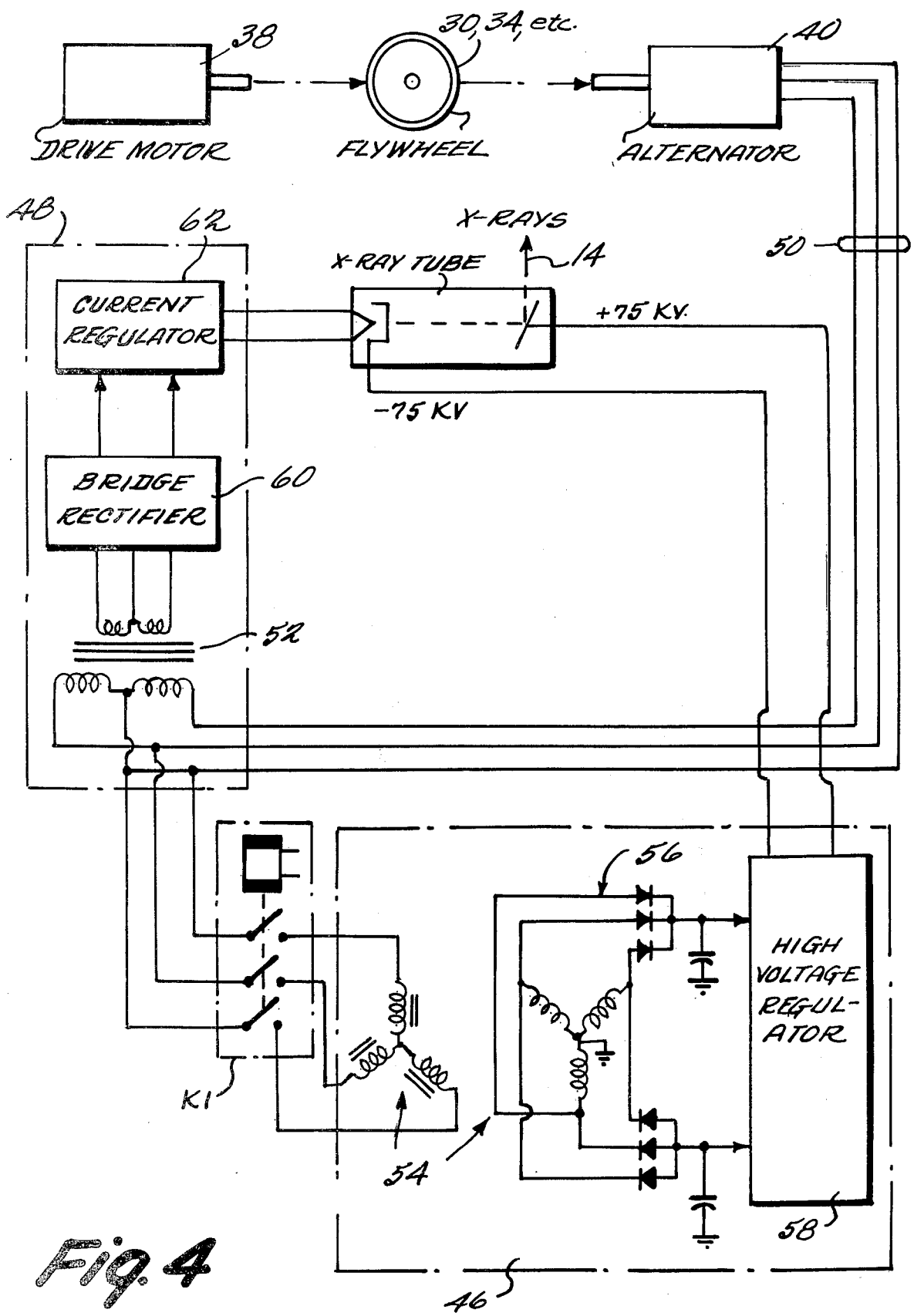
FIG. 4 is an electrical circuit diagram of the system shown in FIGS. 2 and 3.

Now, however, with the exemplary embodiment of this invention shown in FIGS. 2-4, the heavy transformers, heat exchangers, etc., are actually mounted as part of a flywheel assembly for rotation directly with the X-ray source 10. The inertial mechanical energy stored by the rotational motion of this combined mass is then used to provide the electrical energy generated and supplied to the X-ray tube. Not only does this arrangement avoid the necessity for slip rings or cables, it also greatly facilitates rapid scanning cycles where some type of energy storage facility is preferably employed in any event. Furthermore, the relatively large mass of the flywheel (as enhanced by other heavy components mounted thereon), may be used as a heat sink for the various components, in addition to its energy storage capability.

As shown in FIG. 2, the exemplary embodiment of this invention employs a support member 30 mounted for rotational motion as shown by arrow 32. Support member 30 is approximately six meters in diameter with a one meter aperture in the center defining the patient circle 18. In addition, support member 30 is provided with a relatively heavy plate 34 mounted about its outer periphery to, in effect, form a flywheel with a heavy mass concentrated at the maximum diameter thus increasing the potential storage of mechanical inertial energy for any given rotational speed. The flywheel formed by the rotating components is driven through belt 36 by an electrical motor 38. Alternator 40 is driven through belt 42 engaged with a fixed pulley 44.

Other components needed for converting the stored inertial mechanical energy into electrical energy for powering the X-ray tube 10 are also mounted on support plate 30. For example, relay K1, transformer, rectifier and voltage regulator 46, filament transformer and current regulator 48 are all distributed about and mounted upon support member 30. In addition, the heat exchanger for X-ray tube 10 is mounted in conjunction with a counterweight as shown at 50. The positioning of these various components on support member 30 is such that substantially balanced rotational motion of the entire assembly results. Such balanced disposition of the elements can be achieved by conventional mechanical engineering principles as will be appreciated.

The effective moment of inertia for the entire rotating mass shown in FIGS. 2 and 3 may be calculated as the sum of the moments for each of the individual rotating components. Of course, the moment of inertia for any given component is equal to its mass times the square of the effective radius from the center of rotation. For the exemplary dimensions shown in FIGS. 2 and 3, and for the following assumed masses for the various components, the moment of inertia can be calculated as approximately 8,250 $KgM^2$, excluding motor armature inertia:

TABLE I
ASSUMED MASSES

| | |
|---|---|
| X-ray tube assembly 10 | 50 kg |
| Counterweight and heat exchanger 50 | 300 kg |
| Support member 30 and plate 34 (assume an effective radius of 2 meters) | 1,000 kg |
| High voltage transformer, etc., 46 | 350 kg |
| Alternator 40 | 350 kg |

According to well-known laws of physics, the kinetic energy stored in a mass rotating at an angular velocity $\omega$ is equal to half the moment of inertia times the square of the angular velocity. In the exemplary embodiment, a complete revolution must take place in less than a second so as to provide a scanning cycle of less than a second in duration. Accordingly, for purposes of illustration, it will be assumed that the angular velocity is equal to eight radians per second. With this assumption, the stored kinetic energy in the rotating mass of this example will be approximately 250,000 joules. As earlier mentioned, approximately 75,000 joules are required (for statistical reasons) to make a successful tomographic scan cycle. While the example just described would clearly have more than enough stored energy to provide the requisite 75,000 joules, the consequent deceleration of the rotating mass caused by the extraction of approximately one-third of its stored energy might be excessive.

Accordingly, the presently preferred exemplary embodiment provides for an increased mass of the support member 30 and plate 34 of an additional 500 kg. Since most or possibly all of this increased mass would be disposed in the plate 34 about the periphery, the effective radius increases slightly to approximately 2.5 meters. Using this somewhat heavier flywheel, and the same rate of angular rotation, the stored kinetic energy equals approximately 400,000 joules. The mechanical-to-electrical energy conversion process is conservatively assumed to be only approximately 70 percent efficient. Therefore, approximately 108,000 joules of mechanical energy will have to be extracted from the 400,000 that are stored in the rotating mass during any given scan cycle. Assuming a one second scan cycle, the speed of the rotating mass would therefore be expected to drop by approximately 13–14 percent due to the extraction of this mechanical energy. However, at the same time, motor 38 is capable of supplying energy to the system to somewhat reduce this deceleration effect. For example, if motor 38 is assumed to be a 10 horsepower motor, at 50 percent efficiency it will be capable of providing at least 3,750 joules in a one second scan cycle. Accordingly, with this energy input, the rotating mass would probably suffer a speed decrease of only approximately 10–11 percent.

Assuming the same 10 horsepower driving motor 38 is 50 percent efficient, and further allowing approximately one horsepower in the system to overcome frictional effects, wind drag, etc., there remains approximately four horsepower usable for acceleration of the rotating mass. Since the moment of inertia for the rotating mass is approximately 13,000 $KgM^2$ and since the final desired rotational speed is eight radians per second, it is possible to use well-known laws of physics to show that the mass may be accelerated from 0 to its final speed in approximately 35 seconds. Such rapid acceleration is actually unnecessary because the rotating mass may be left in continuous rotation between scans. Accordingly, one could employ a smaller-sized driving motor 38 if desired. In addition, the mass of the rotating assemblage could be further increased to reduce the deceleration effect encountered during the scan cycle.

In the example just described, if the 10 horsepower driving motor 38 is a three-phase alternating current motor rated at 1,800 revolutions per minute, then it will require approximately 7,500 watts of electrical input or approximately 2,500 watts per phase. If the input voltage is 208 volts per phase, then the amperage drawn by the motor during full load conditions is approximately 12 amps per phase, thus permitting the assemblage to be driven with a 15-amp three-phase 220 volt circuit.

The electrical schematic for the exemplary embodiment of FIGS. 2 and 3 is shown in FIG. 4. As earlier described, drive motor 38 mechanically rotates the flywheel assemblage 30, 34, etc., from which the alternator 40 extracts mechanical energy. As will be explained below, this extraction process may be selectively disabled during stand-by conditions so as to minimize the amount of power required from drive motor 38. A 230 volt three-phase 400 Hz. output from alternator 40 is connected via output lines 50 to the primary of filament transformer 52 and high voltage transformer 54. The contacts of relay K1 are interposed in the connections to the primary of high voltage transformer 54 so as to disconnect this major portion of the load on alternator 40 during stand-by conditions. Of course, this disconnection also has the effect of stopping the generation of X-rays from X-ray tube 10 during stand-by conditions. The output from the secondary of the high voltage transformer 54 is rectified by a three-phase full wave rectifier 56 and passed through voltage regulator 58 to supply the requisite high voltage potential between the cathode and anode of a conventional X-ray tube 10. The voltage regulator 58 should be designed according to conventional practice so as to substantially eliminate any "droop" in its voltage output caused by the approximately 10 percent loss of flywheel speed during a scan cycle and the consequent approximately 10 percent loss of output power from alternator 40 during this same period. In addition and/or alternatively, another inductor or the high voltage transformer 54 may itself be made resonant at a frequency slightly below the nominal 400 Hz. output of alternator 40. If such a resonant transformer is employed, then as the output frequency of alternator 40 decreases during deceleration of the flywheel, the output of the transformer will nevertheless tend to be maintained at a constant value due to the approaching resonance condition at such a reduced frequency of operation. A ferro-resonant voltage regulation transformer (available under the trade name SOLA) may be used if tuned to resonate at approximately 360 Hz. in the exemplary embodiment.

The filament transformer 52 is shown as continuously connected to the output of alternator 40 since it is assumed that the filament of the X-ray tube 10 will be kept hot even during stand-by conditions. However, as will be appreciated, a suitable switch or relay arrangement may be provided for disconnecting this load from alternator 40 as well during extended stand-by conditions. The output from filament transformer 52 is also rectified in a three-phase rectifier 60 and supplied to the filament of X-ray tube 10 through a current regulator 62 which is designd to substantially prevent any "droop" in the filament current of the X-ray tube during the expected deceleration of the flywheel during a scan cycle.

Figure 5:
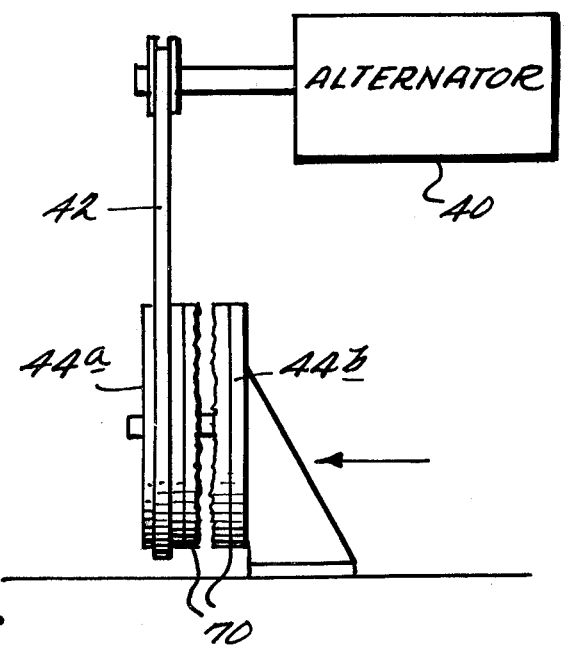
FIG. 5 is a schematic showing of an additional or alternative means for at least partially disabling the conversion means during stand-by operation thus conserving energy required for maintaining desired rotational speed.

Besides the selective disconnection of electrical load from alternator 40, the mechanical input to the alternator may also be effectively disconnected during stand-by conditions as shown in FIG. 5. Here, the belt drive 42 for alternator 40 is connected to a pulley 44a which may be selectively engaged with a relatively fixed clutch plate 44b. The circular clutch faces 70 may be engaged by pushing the rotationally fixed clutch plate 44b to the left (either manually or through a solenoid arrangement, etc.) so as to brake pulley 44a and thus provide a mechanical input to alternator 40 just prior to a scan cycle when it is desired to turn on the filament of the X-ray tube. Subsequently, relay K1 would be operated so as to fully energize the X-ray tube with the requisite high voltage and cause the generation of X-ray beam 14. It may also be possible to eliminate relay K1 and to simply engage clutch faces 70 to begin the generation of both filament and high voltage power for X-ray tube 10, although in this case, some means would probably have to be provided to absorb and shield the X-rays from a patient until the full steady output of the X-ray tube is achieved.

The relatively rapid deceleration of a large rotating mass in this invention may produce relatively large forces between the entire scanning machine and its mount to a stationary surface such as the floor of a building or the like. If these forces are sufficiently large, it may be advantageous to employ two counter rotating flywheels so that this type of torque which results from one flywheel will be approximately cancelled by a similar torque resulting from deceleration of the oppositely rotating flywheel. The two flywheels would preferably be geared or otherwise drivingly engaged one with another and rotating about the same axis, although it may be possible to offset the flywheels along parallel axes of rotation. The two flywheels should be designed to store approximately the same amounts of kinetic energy. Th energy conversion, X-ray tube and other relatively large rotating components may be mounted on either flywheel or, alternatively, a counter-rotating flywheel, per se, may be employed to produce the requisite counteracting torque.

While only one exemplary embodiment of this invention has been described in detail, those skilled in the art will appreciate that there are many possible modifications and variations of this exemplary embodiment which still employ the novel and advantageous features of this invention. Accordingly, all such modifications and variations are intended to be included within the scope of the following claims.

What is claimed is:

1. A tomographic scanner of a type which utilizes a rotating source of radiation, said scanner comprising:
   a rotationally mounted support member;
   drive means for rotating said support member;
   an electrically activated source of radiation mounted for rotation with said support member; and
   conversion means also mounted for rotation with said support member for converting at least some of the inertial mechanical energy of the rotating apparatus into electrical energy sufficient to activate said source of radiation during a scan cycle of the tomographic scanner.

2. A tomographic scanner as in claim 1 wherein said support member is weighted at its periphery to increase the amount of inertial mechanical energy stored therein during rotational motion.

3. A tomographic scanner as in claim 1 wherein said support member is adapted to transfer heat away from at least said source of radiation.

4. A tomographic scanner as in claim 1 wherein:
   said source of radiation comprises an X-ray tube; and
   said conversion means comprises a mechanically driven electrical alternator, a transformer and a rectifier connected for supplying high voltage electrical energy to said X-ray tube.

5. A tomographic scanner as in any of claims 1, 2, 3 or 4 wherein said conversion means includes means for at least partially disabling the conversion means during stand-by conditions thereby conserving the energy required from said drive means for maintaining a desired rotational speed of said support member.

6. A tomographic scanner as in claim 5 wherein said means for at least partially disabling comprises at least one of:
   a selectively operated electrical switch or relay means for selectively reducing the electrical load connected to the conversion means; and
   a selectively operated clutch means for decoupling the conversion means from its mechanical drive.

7. A tomographic scanner as in any of claims 1, 2, 3 or 4 wherein said conversion means includes:
   regulation means for reducing the change in electrical output which would otherwise occur during a scan cycle as the support member slows its rotational speed in response to the extraction of mechanical energy therefrom.

8. A tomographic scanner as in claim 7 wherein said regulation means comprises a voltage regulator connected to maintain at least one output voltage of the conversion means within predetermined limits of change from a predetermined value during a scan cycle.

9. A tomographic scanner as in any of claims 1, 2, 3 or 4 wherein said conversion means and said source of radiation comprise a plurality of physically separate components having a substantial weight which are disposed on said support member so as simultaneously to cause substantial storage of inertial energy in said components which rotate with the support member and to balance same for smooth rotational motion.

10. A tomographic scanner as in claims 1, 2, 3 or 4 wherein said conversion means comprises an electrical alternator having a pulley which is driven by a flexible continuous member engaged with another pulley fixed relative to the rotating support member.

11. In a tomographic scanner of a type which utilizes a rotating source of penetrating radiation, an improvement characterized by:
a rotating electrically operated source of penetrating radiation; and
mechanical-to-electrical energy conversion means mounted for rotation with said source of penetrating radiation and connected to supply said source with electrical energy derived, at least in part, by converting inertial mechanical energy stored in the rotating conversion means itself into said electrical energy.

12. An improved tomographic scanner as in claim 11 further comprising a rotationally mounted flywheel on which said source and said energy conversion means are mounted, said flywheel also storing inertial mechanical energy when rotated which is, at least in part, also converted by said conversion means into electrical energy and supplied to said source.

13. An improved tomographic scanner as in claim 12 wherein said flywheel also provides a heat sink for at least said source.

14. An improved tomographic scanner as in claim 11 or 12 wherein said conversion means includes means for at least partially disabling it during stand-by conditions thereby conserving the mechanical energy required to maintain a desired rotational speed of the rotating apparatus.

15. An improved tomographic scanner as in claim 14 wherein said means for at least partially disabling comprises at least one of:
a selectively operated electrical switch or relay means for selectively reducing the electrical load connected to the conversion means; and
a selectively operated clutch means for decoupling the conversion means from its mechanical drive.

16. An improved tomographic scanner as in claim 11 or 12 wherein said conversion means includes:
regulation means for reducing the change in electrical output which would otherwise occur as the rotating apparatus slows its rotational speed due to the extraction of mechanical energy therefrom.

17. An improved tomographic scanner as in claim 16 wherein said regulation means comprises a voltage regulator connected to maintain at least one output voltage of the conversion means within predetermined limits of change from a predetermined value.

18. An improved tomographic scanner as in claim 11 or 12 wherein said conversion means comprises a plurality of physically separate components having substantial weight which are disposed relative to one another and to said source so as simultaneously to cause substantial storage of inertial energy therein and to balance same for smooth rotational motion.

19. An improved tomographic scanner as in claim 11 or 12 wherein said conversion means comprises an electrical alternator having a pulley driven by a flexible continuous member engaged with another pulley which is fixed relative to the rotating apparatus.

20. An improved tomographic scanner as in claim 11 or 12 wherein the rotating apparatus is continuously rotated so as to maintain stored mechanical energy sufficient to operate said source during one or more selected revolutions and thereby provide a relatively rapid tomographic scan cycle.

21. An improved tomographic scanner as in claim 20 wherein said scan cycle is on the order of one second or less in duration.

22. Apparatus for generating a rotating beam of penetrating radiation directed inwardly towards the axis of rotation, said apparatus comprising:
an electrically operated source of penetrating radiation mounted for rotation about an axis, said source being disposed to provide a beam of penetrating radiation directed inwardly towards said axis; and
mechanical-to-electrical energy conversion means mounted for rotation with said source of penetrating radiation and connected to supply said source with electrical energy derived, at least in part, by converting inertial mechanical energy into said electrical energy.

23. Apparatus as in claim 22 further comprising a rotationally mounted flywheel on which said source and said energy conversion means are mounted, said flywheel also storing inertial mechanical energy when rotated which is, at least in part, also converted by said conversion means into electrical energy supplied to said source.

24. Apparatus as in claim 23 wherein said flywheel also provides a heat sink for at least said source.

25. Apparatus as in claim 22 or 23 wherein said conversion means includes means for at least partially disabling it during stand-by conditions thereby conserving the mechanical energy required to maintain a desired rotational speed of the rotating apparatus.

26. Apparatus as in claim 25 wherein said means for at least partially disabling comprises at least one of:
a selectively operated electrical switch or relay means for selectively reducing the electrical load connected to the conversion means; and
a selectively operated clutch means for decoupling the conversion means from its mechanical drive.

27. Apparatus as in claim 22 or 23 wherein said conversion means includes:
regulation means for reducing the change in electrical output which would otherwise occur as the rotating apparatus slows its rotational speed due to the extraction of mechanical energy therefrom.

28. Apparatus as in claim 27 wherein said regulation means comprises a voltage regulator connected to maintain at least one output voltage of the conversion means within predetermined limits of change from a predetermined value.

29. Apparatus as in claim 22 or 23 wherein said conversion means comprises a plurality of physically separate components having substantial weight which are disposed relative to one another and to said source so as simultaneously to cause substantial storage of inertial energy therein and to balance same for smooth rotational motion.

30. Apparatus as in claim 22 or 23 wherein said conversion means comprises an electrical alternator having a pulley driven by a flexible continuous member engaged with another pulley which is fixed relative to the rotating apparatus.

31. Apparatus as in claim 22 or 23 wherein the rotating apparatus is continuously rotated so as to maintain stored mechanical energy sufficient to operate said source during one or more selected revolutions thereby rapidly scanning said beam about said axis at a multiplicity of angles.

32. Apparatus as in claim 31 wherein said beam is scanned through one complete revolution in a time period on the order of one second or less in duration.

33. A method of generating a rotating beam of penetrating radiation directed inwardly towards the axis of rotation for use in a tomographic scanner, said method comprising the steps of:
continuously rotating an electrically operated source of penetrating radiation about the axis of a tomographic scanner, said source being disposed to provide a beam of penetrating radiation directed inwardly towards said axis;
continuously rotating additional components whereby substantial inertial mechanical energy is stored in such rotating components;
converting, during one or more selected time periods, a portion of said stored mechanical energy to electrical energy suitable for, at least in part, energizing said source; and
energizing said source with said converted electrical energy.

34. A method as in claim 33 wherein:
said converting step is performed on a rotating support member to which said source and said additional components are also affixed.

35. A method as in claim 34 wherein at least some of said additional components are utilized in said converting step.

36. A method as in claim 33, 34 or 35 wherein said converting step is at least partially discontinued during stand-by conditions thereby conserving the mechanical energy required to maintain a desired rotational speed.

37. A method as in claim 36 wherein said at least partially discontinuing step comprises at least one of the steps of:
selectively reducing the connected electrical load;
selectively decoupling the mechanical input from the apparatus used in said converting step.

38. A method as in claim 33, 34 or 35 wherein said energizing step causes said beam to be produced during a tomograhic scanning cycle comprising on the order of one revolution of said source which occurs in approximately one second or less.

* * * * *